(12) United States Patent
Plambech et al.

(10) Patent No.: US 12,156,991 B2
(45) Date of Patent: Dec. 3, 2024

(54) INJECTION SYSTEMS FOR DRUG DELIVERY WITH INTERNAL FORCE TRANSMISSION

(71) Applicant: AMGEN INC., Thousand Oaks, CA (US)

(72) Inventors: Christian Plambech, Soeborg (DK); Matias Melander, Copenhagen (DK)

(73) Assignee: AMGEN INC., Thousand Oaks, CA (US)

( * ) Notice: Subject to any disclaimer, the term of this patent is extended or adjusted under 35 U.S.C. 154(b) by 710 days.

(21) Appl. No.: 16/590,636

(22) Filed: Oct. 2, 2019

(65) Prior Publication Data

US 2020/0101229 A1 Apr. 2, 2020

Related U.S. Application Data

(60) Provisional application No. 62/740,232, filed on Oct. 2, 2018.

(51) Int. Cl.
*A61M 5/20* (2006.01)
*A61M 5/315* (2006.01)
*A61M 5/32* (2006.01)

(52) U.S. Cl.
CPC ...... *A61M 5/2033* (2013.01); *A61M 5/31568* (2013.01); *A61M 5/31585* (2013.01);
(Continued)

(58) Field of Classification Search
CPC ............ A61M 5/2033; A61M 5/31585; A61M 5/3157; A61M 2005/208; A61M 2005/2086; A61M 2005/3267
See application file for complete search history.

(56) References Cited

U.S. PATENT DOCUMENTS 6,102,896 A 8/2000 Roser
10,722,655 B2 7/2020 Folk et al.
(Continued)

FOREIGN PATENT DOCUMENTS

CN 106413779 A 2/2017
CN 107427836 A 12/2017
(Continued)

OTHER PUBLICATIONS

International Application No. PCT/US2019/054189, International Search Report and Written Opinion, dated Dec. 18, 2019.
(Continued)

*Primary Examiner* — Nathan R Price
*Assistant Examiner* — Tania Ismail

(57) ABSTRACT

Injection systems for drug delivery are disclosed. A system may include a container filled or fillable with a drug, a stopper movably disposed in the container, a plunger, an energy source outputting a force, a mechanical linkage operable to transmit the force output by the energy source to the plunger to cause the plunger to act on the stopper to expel the drug from the container, and a trigger member. The system may have pre-injection state where the trigger member inhibits actuation of the mechanical linkage, an injection state where the trigger member permits actuation of the mechanical linkage, and a post-injection state where the plunger is stationarily positioned in an end-of-dose position. The system may be designed to limit the number of components included in various force transmission loops present in the pre-injection, injection, and/or post-injection states.

29 Claims, 10 Drawing Sheets

(52) U.S. Cl.
CPC ............... *A61M 2005/2013* (2013.01); *A61M 2005/208* (2013.01); *A61M 2005/2086* (2013.01); *A61M 5/3157* (2013.01); *A61M 2005/3267* (2013.01)

(56) References Cited

U.S. PATENT DOCUMENTS

| | | | |
|---|---|---|---|
| 11,305,061 | B2 | 4/2022 | Grimoldby et al. |
| 2003/0114789 | A1 | 6/2003 | Haar et al. |
| 2005/0154346 | A1 | 7/2005 | Green |
| 2011/0106008 | A1 | 5/2011 | Kronestedt |
| 2011/0213314 | A1 | 9/2011 | Guillermo |
| 2013/0035634 | A1 | 2/2013 | Cappello et al. |
| 2013/0046233 | A1* | 2/2013 | Green ............... A61M 5/3159 604/68 |
| 2013/0317448 | A1 | 11/2013 | Hourmand et al. |
| 2014/0243741 | A1 | 8/2014 | Kaufmann et al. |
| 2016/0008549 | A1 | 1/2016 | Plumptre et al. |
| 2016/0038677 | A1 | 2/2016 | Kiilerich |
| 2016/0067419 | A1 | 3/2016 | Morris |
| 2016/0074588 | A1 | 3/2016 | Butler |
| 2017/0043098 | A1 | 2/2017 | Kohlbrenner et al. |
| 2018/0110926 | A1 | 4/2018 | Schrul et al. |
| 2019/0247587 | A1 | 8/2019 | Kohlbrenner |

FOREIGN PATENT DOCUMENTS

| | | |
|---|---|---|
| CN | 106794305 B | 2/2021 |
| EP | 2438947 A1 | 4/2012 |
| JP | 2006500150 A | 1/2006 |
| JP | 2015521055 A | 7/2015 |
| TW | 201212970 A | 4/2012 |
| TW | 201718043 A | 6/2017 |
| TW | 201818987 A | 6/2018 |
| WO | WO-2004/011066 A1 | 2/2004 |
| WO | WO-2012000873 A1 | 1/2012 |
| WO | WO-2016124908 A1 | 8/2016 |
| WO | WO-2017/187177 A1 | 11/2017 |
| WO | WO-2017209899 A1 | 12/2017 |
| WO | WO-2018226565 A1 * | 12/2018 ............... A61M 5/20 |

OTHER PUBLICATIONS

Chinese Patent Application No. 2019800643416, Office Action, dated Jul. 18, 2022.
Chinese Patent Application No. 2019800643416, Second Office Action, dated Mar. 18, 2023.
Office Action received in counterpart Argentinian Patent Application No. P190102801, dated May 18, 2023.
Office Action received in counterpart Taiwanese Patent Application No. 108135651, dated May 9, 2023.
Notice of Allowance received in counterpart Chinese Application No. 2019800643416, dated Aug. 4, 2023.
Office Action received in counterpart Japanese Application No. 2021-517871, dated Aug. 29, 2023.
Examination Report received in counterpart European Patent Application No. 19790378.4, dated Nov. 27, 2023.
Office Action received in counterpart R.O.C. Patent Application No. 108135651, dated Oct. 19, 2023.
Office Action received in counterpart Israel Patent Application No. 281712, dated Dec. 21, 2023.
Office Action received in counterpart Japanese Patent Application No. 2021-517871, dated Mar. 5, 2024.
Examination Report received in counterpart Australian Patent Application No. 2019352616, dated Jun. 12, 2024.
First Office Action received in counterpart Mexican Patent Application No. MX/a/2021/003492, dated Jul. 24, 2024.

* cited by examiner

INJECTION SYSTEMS FOR DRUG DELIVERY WITH INTERNAL FORCE TRANSMISSION

CROSS-REFERENCE TO RELATED APPLICATION

Priority is claimed to U.S. Provisional Patent Application No. 62/740,232, filed Oct. 2, 2018, the entire contents of which are hereby incorporated by reference.

FIELD OF DISCLOSURE

The present disclosure generally relates to injection systems for drug delivery and, more particularly, managing internal forces generated within such systems.

BACKGROUND

Injectable drugs are conventionally administered through the use of a needle attached to a syringe. The needle is manually inserted into a patient's tissue, and a plunger is then manually displaced to eject a drug from a reservoir into the patient. Use of a syringe to self-administer a drug can be cumbersome and/or uncomfortable for certain patients, particularly those having little or no experience with operating syringes. As such, patients often resort to automated injection systems to assist with the injection. Such systems generally provide the actuation energy necessary to insert the needle or cannula and/or expel the drug from the reservoir.

Storing and/or releasing actuation energy creates mechanical stress in various components of the injection system. The stress can be significant, particularly in applications involving the injection of a high viscosity drug. Further, the stress may be present before, during, and even after the injection takes place. To ensure that such stress does not compromise the integrity of the injection system, it may be necessary to construct various components within certain design parameters, including, for example, having no less than a certain thickness and/or material strength. Typically the outer casing or housing of the injection system is required to bear at least some of the stress. This can place limitations on the shape and/or material used for the outer casing, which in turn can affect the patient/user experience.

As set forth in more detail below, the present disclosure sets forth injection systems embodying advantageous alternatives to the existing injection systems, and that may address one or more of the challenges or needs mentioned herein, as well as provide other benefits and advantages.

SUMMARY

One aspect of the present disclosure provides a system for injecting a drug. The system may include an outer housing defining an interior space and configured, in some embodiments, to be held by a patient or user during an injection. A container may be disposed or disposable in the interior space of the outer housing, and may be filled or fillable with the drug. A stopper may be movably disposed in the container for expelling the drug from the container. The system may include a drive assembly including a plunger for acting on the stopper, an energy source outputting or operable to output a force, and a mechanical linkage operable to transmit the force output by the energy source to the plunger to cause the plunger to act on the stopper to expel the drug. A trigger member may selectively engage the mechanical linkage to control actuation of the mechanical linkage. In a pre-injection state, the trigger member may inhibit actuation of the mechanical linkage; whereas, in an injection state, the trigger member may permit actuation of the mechanical linkage. The system may also have a post-injection state wherein the plunger is stationarily positioned in an end-of-dose position. The outer housing may be configured so that it is substantially free of or does not bear any load caused by the force output by the energy source in the pre-injection state, the injection state, and/or the post-injection state.

Another aspect of the present disclosure provides a system for injecting a drug. The system may include a container filled or fillable with the drug, and a stopper movably disposed in the container for expelling the drug from the container. The system may include a drive assembly including a plunger for acting on the stopper, an energy source outputting or operable to output a force, and a mechanical linkage operable to transmit the force output by the energy source to the plunger to cause the plunger to act on the stopper to expel the drug. A trigger member may selectively engage the mechanical linkage to control actuation of the mechanical linkage. In a pre-injection state, the trigger member may inhibit actuation of the mechanical linkage; whereas, in an injection state, the trigger member may permit actuation of the mechanical linkage. The system may also have a post-injection state wherein the plunger is stationarily positioned in an end-of-dose position. In the pre-injection state, at least the energy source, the plunger, the mechanical linkage, and the trigger member may be operably connected in series to define a first force transmission loop, and wherein the first force transmission loop directly or indirectly receives the force output by the energy source.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

DETAILED DESCRIPTION

Figure 1:
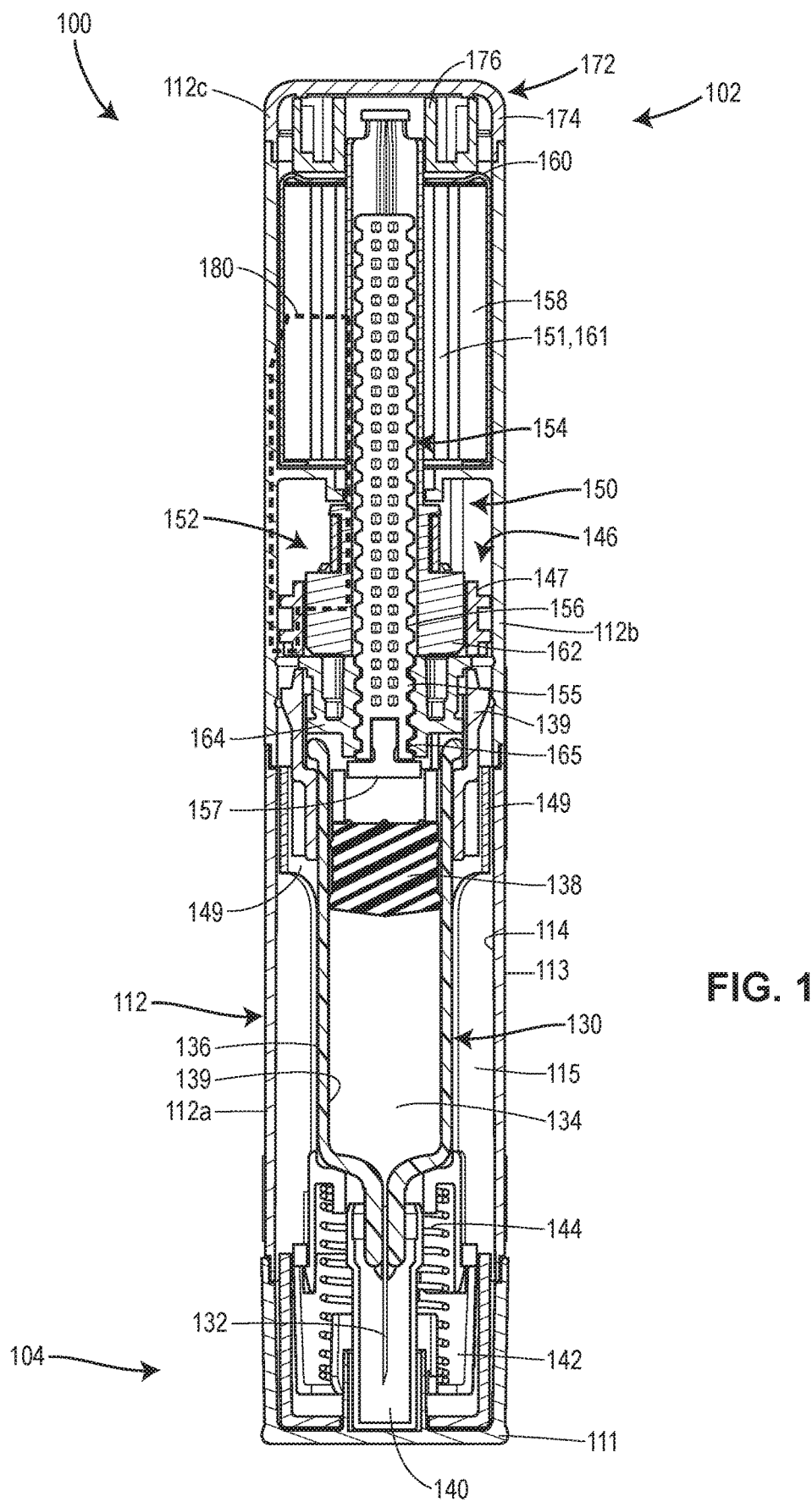
FIG. 1 is a cross-sectional view of an injection system for drug delivery in a pre-injection state according to an embodiment of the present disclosure, and illustrating a first force transmission loop within the system.

The present disclosure generally relates to the configuration and operation of an injection system for drug delivery. While most embodiments are described in the context of a hand-held injector such as autoinjector, the scope of the present disclosure in not limited to such injectors. Other injection systems for which the present disclosure is applicable include, without limitation, wearable injectors such as on-body injectors which adhere (e.g., via an adhesive) to a patient's skin, ambulatory pumps worn on a patient's clothing, and hybrid autoinjector/on-body injectors.

In general, the injection systems of the present disclosure are designed to limit the number of parts or components put under mechanical stress or load as a result of a force output by an energy source. The group or groups of components which are placed under mechanical stress or load may vary depending on whether the injection system is in a pre-injection state, an injection state, or a post-injection system. By excluding or shielding, in one or more states, certain components from the force output by the energy source, such components may be subject to less restrictive design parameters, and, as such, more options may be available for their design. For example, such components may be manufactured with less material and/or with lighter materials, and/or their shape or configuration may not be dictated by mechanical stress considerations. This freedom may also allow for a greater variety of exterior form factors to meet patient needs or preferences, and in certain cases, provide cost savings too. Furthermore, excluding certain components from having to bear a mechanical stress or load in a pre-injection state may provide flexibility in how such components are assembled. For example, certain components may be assembled and loaded to form a force transmission loop prior to a final assembly stage. This simplifies the final assembly stage and potentially allows it to be performed at a facility that is less costly or demanding to maintain than a facility where the earlier manufacturing steps are performed. Other benefits and advantages are also possible and will be apparent to one of ordinary skill in the art reviewing the present disclosure.

Referring now to FIGS. 1-3B, illustrated are several cross-sectional views of an embodiment of a system 100 for injecting a drug, which may also be referred to herein as a medicament or drug product. The drug may be, but is not limited to, various biologicals such as peptides, peptibodies, or antibodies. The drug may be in a fluid or liquid form, although the disclosure is not limited to a particular state. In certain liquid formulations, the drug may have a relatively high viscosity.

Various implementations and configurations of the system 100 are possible. The system 100 may be configured as a single-use, disposable injector, or alternatively, a multiple-use reusable injector. The system 100 may be configured as an autoinjector for self-administration by a patient, although the system 100 can also be used by a caregiver or a formally trained healthcare provider (e.g., a doctor or nurse) to administer an injection. In embodiments where the system 100 is configured as an autoinjector or pen-type injector, the system 100 may be held in the hand of a patient or user over the duration of drug delivery, also referred to herein as dosing. In alternative embodiments, where drug delivery may be delayed or take several minutes or hours to complete, the system 100 may be configured as an on-body injector which is releasably attached to the patient's skin via, for example, an adhesive disposed at or applied to an exterior surface of the system 100.

The configuration of various components included in the system 100 may depend on the operational state of the system 100. The system 100 may have a pre-injection or storage state, an injection state, and a post-injection state, although fewer or more states are also possible. The pre-injection state may correspond to the configuration of the system 100 following assembly and prior to activation by a patient or user (e.g., activation of an energy source of the system 100). The pre-injection state may exist in the time between when the system 100 leaves a manufacturing facility and when a patient or user activates the system 100 for drug delivery. The injection state may correspond to the configuration of the system 100 over the course of drug delivery. In certain embodiments, the injection state may also exist in the time between activation and drug delivery, during which a needle or other delivery member is inserted into the patient. The post-injection state may correspond to the configuration of the system 100 after drug delivery is complete and/or when a stopper is arranged in an end-of-dose position within a container.

FIG. 1 illustrates the system 100 in a pre-injection state. The system 100 includes a proximal end 102 and a distal end 104, with the distal end 104 being defined by a cap 111 in the pre-injection state. The cap 111 may be removably attached to an outer casing or housing 112. Prior to use, a patient or user may detach the cap 111 from the outer housing 112 to expose an opening providing access to a subcutaneous delivery member such as a needle or cannula. In the illustrated embodiment, the outer housing 112 is constructed in three separate (i.e., discrete) and rigidly connected components, arranged from the distal end 104 to proximal end 102 as follows: a front housing portion 112a, a rear housing portion 112b, and a rearmost housing portion 112c. By way of their rigid connection, the housing portions 112a, 112b, and 112c may be prevented from moving relative to each other. In some versions, the housing portions 112a, 112b, and 112c may be made of different materials and/or thickness depending on the amount of load, if any, that they bear in the pre-injection, injection, and/or post-injection state. In alternative embodiments, the housing portions 112a, 112b, and 112c may be integrally formed with each other such that the housing portions 112a, 112b, and 112c form a single, unitary structure.

The outer housing 112 may include an exterior surface 113 configured to be held by a patient or user over the course of an injection, and an interior surface 114 defining a hollow interior space 115 in which various moving components are disposed. The outer housing 112 may generally have an elongate shape such as a hollow cylinder or tube, or any other suitable shape.

The system 100 may also include a container 130 that is filled (e.g., pre-filled) or fillable (e.g., filled by a patient or user at the time of use of the system 100) with a drug. The container 130 is disposed or disposable within the interior space 115 of the outer housing 112, particularly the front housing portion 112a. The container 130 may be pre-loaded within the interior space 115 by a manufacturer, or loaded within the interior space 115 by a patient or user at the time of use. In the present embodiment, the container 130 is configured as pre-filled syringe having a staked and rigid hollow needle 132 protruding from its distal end. The needle 132 is connected in fluid communication with an internal bore or reservoir 134 of the container 130. In alternative embodiments, the container 130 may be configured as a cartridge that is not initially in fluid communication with the needle 132 or other subcutaneous delivery member. Instead, the subcutaneous delivery member and/or a fluid pathway connection assembly may be actuated upon activation of the system 100 in order to establish fluid communication between the reservoir 134 and the subcutaneous delivery member. In addition to or as an alternative to the needle 132, in some embodiment a flexible cannula may be included. Whereas the needle 132 may be constructed of a rigid material such as metal, the flexible cannula may be constructed of a relatively soft material such as plastic.

The needle 132 may include a hollow interior passageway extending between its proximal and distal ends to allow the drug to flow through the needle 132 during an injection. An opening, or multiple openings, may be formed in the distal end of the needle 132 to permit the drug to be delivered subcutaneously to the patient. Furthermore, the distal end of the needle 132 may include a tapered region where the width of the subcutaneous delivery member 42 gradually decreases to a tip. The tip may be sharp enough to pierce at least through the patient's skin and subcutaneous tissue. In some versions, the tip may be sharp enough to penetrate through other tissue as well, including, for example, muscle, arterial walls, and/or bone. A removable shield 140 (e.g., a rigid needle shield) may be removably attached to the container 130 and enclose the distal end of the needle 132, including its tip, to maintain the distal end of the needle 132 in a sterile state prior to use. The removable shield 140 may be connected to the cap 111 such that removal of the cap 111 results in detachment of the removable shield 140 from the container 130, thereby exposing the distal end of the needle 132.

Figure 3A:
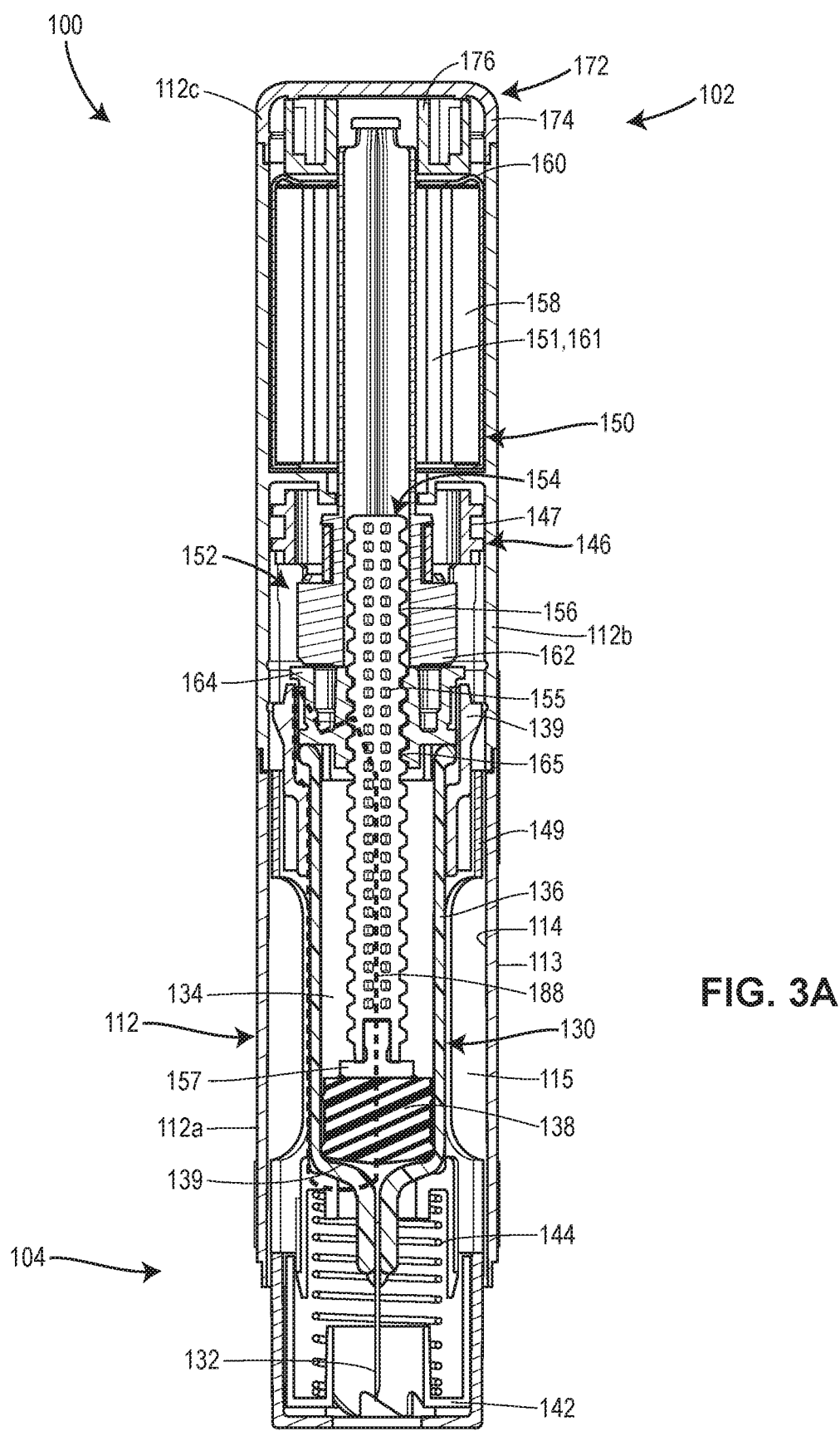
FIG. 3A is a cross-sectional view of the embodiment of the injection system of FIG. 1 in a post-injection state, and depicting a fifth force transmission loop within the system.
Figure 3B:
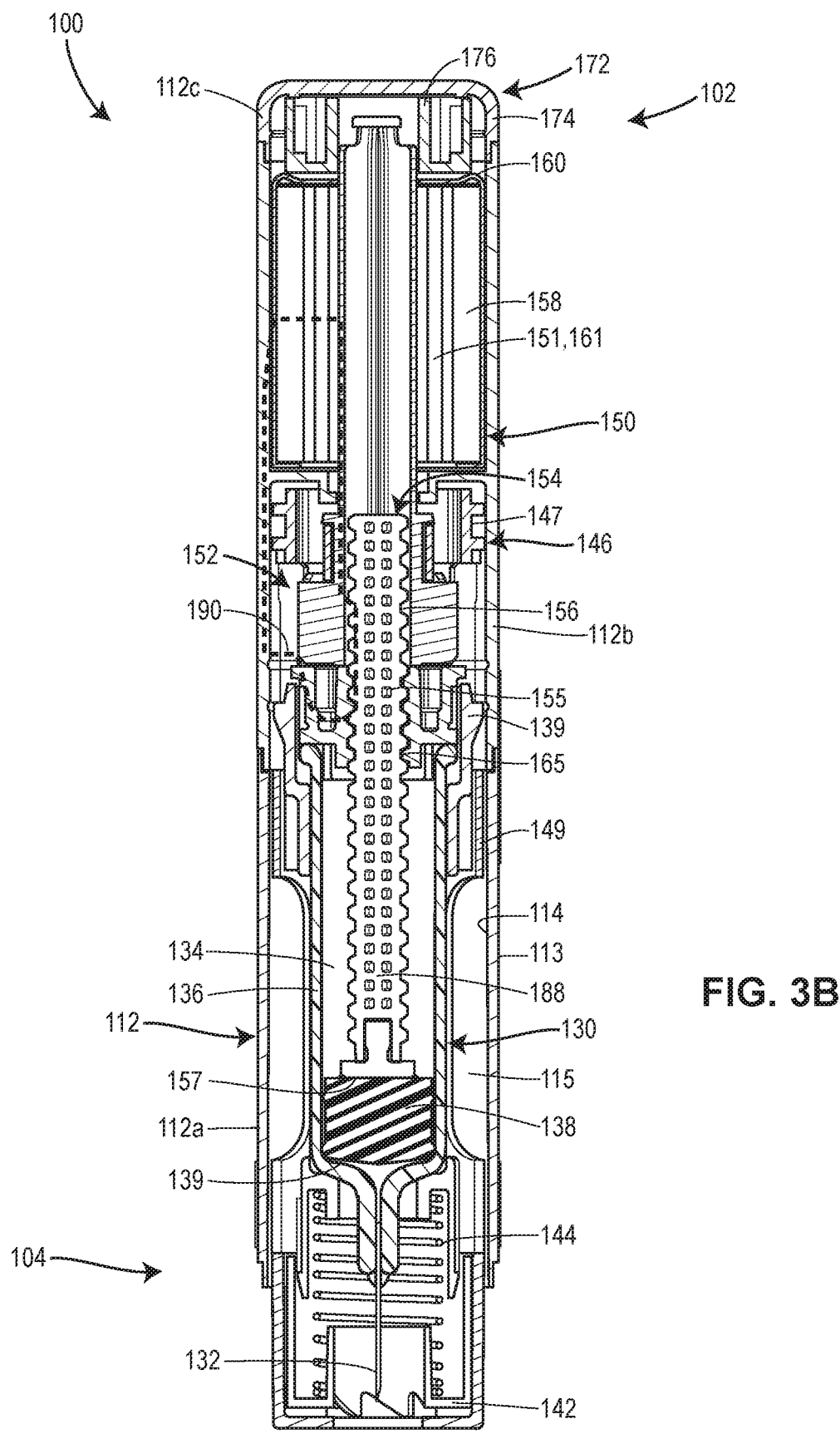
FIG. 3B is a cross-sectional view of the embodiment of the injection system of FIG. 1 in the post-injection state, and illustrating a sixth force transmission loop within the system.

Still referring to FIG. 1, the container 130 may include a rigid wall 136 defining the internal bore or reservoir 134. The wall 136 may be made of glass or plastic. In addition to containing the drug, the reservoir 134 may contain a stopper 138. The stopper 138 may be movably disposed within the container 130 such that it can move in a distal direction along a longitudinal axis of the container 130 from a proximal end of the reservoir 134 to a distal end of the reservoir 134. The stopper 138 may slidably and sealingly contact an interior surface 139 of the wall 136 such that the drug is prevented or inhibited from leaking past the stopper 138 while the stopper 138 is in motion. As a consequence, the stopper 138 is able to expel the drug contained in the reservoir 134 through the needle 132 as the stopper 138 is driven in the distal direction. The proximal end of the container 130 may be open to allow a plunger 154 to extend into the container 30 and push the stopper 138 in the distal direction. The stopper 138 may continue to move in the distal direction until it contacts a proximally-facing portion of the interior surface 139 of the wall 136, as illustrated in FIGS. 3A and 3B. This position of the stopper 138 may be referred to as the end-of-dose position and may correspond to when delivery of the drug to the patient is complete. The stopper 138 may be constructed of rubber or any other suitable material.

As illustrated in FIG. 1, the container 130 may be received, partially or fully, within a carrier or container holder 139. The container holder 139 generally serves as a mount for the container 130, and may be rigidly connected to the container 130 such that the container 130 and the container holder 139 do not move relative to each other during operation of the system 100. Additionally, in certain embodiments, the container holder 139 may be rigidly mounted to the front housing portion 112a, such that the container holder 139 and the front housing portion 112a also do not move relative to each other during operation of the system 100. In alternative embodiments, the container 130 and/or the container holder 139 may move relative to the front housing portion 112a during operation of the system 100. The container holder 139 may have a hollow and generally cylindrical or tubular shape, and it may have various openings or cut-outs formed in its circumferential wall.

Figure 2A:
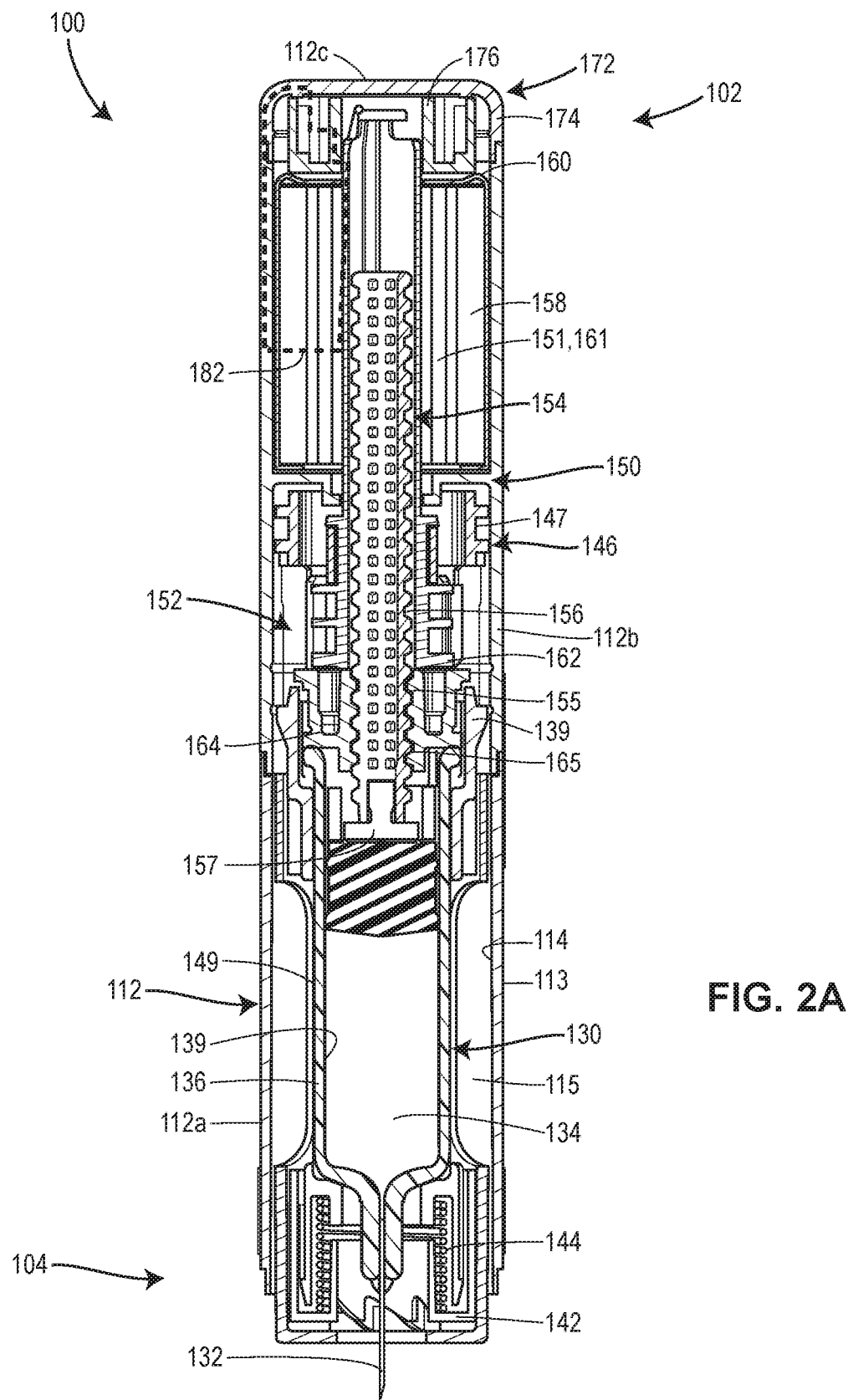
FIG. 2A is a cross-sectional view of the embodiment of the injection system of FIG. 1 in an injection state, and depicting a second force transmission loop within the system.
Figure 2B:
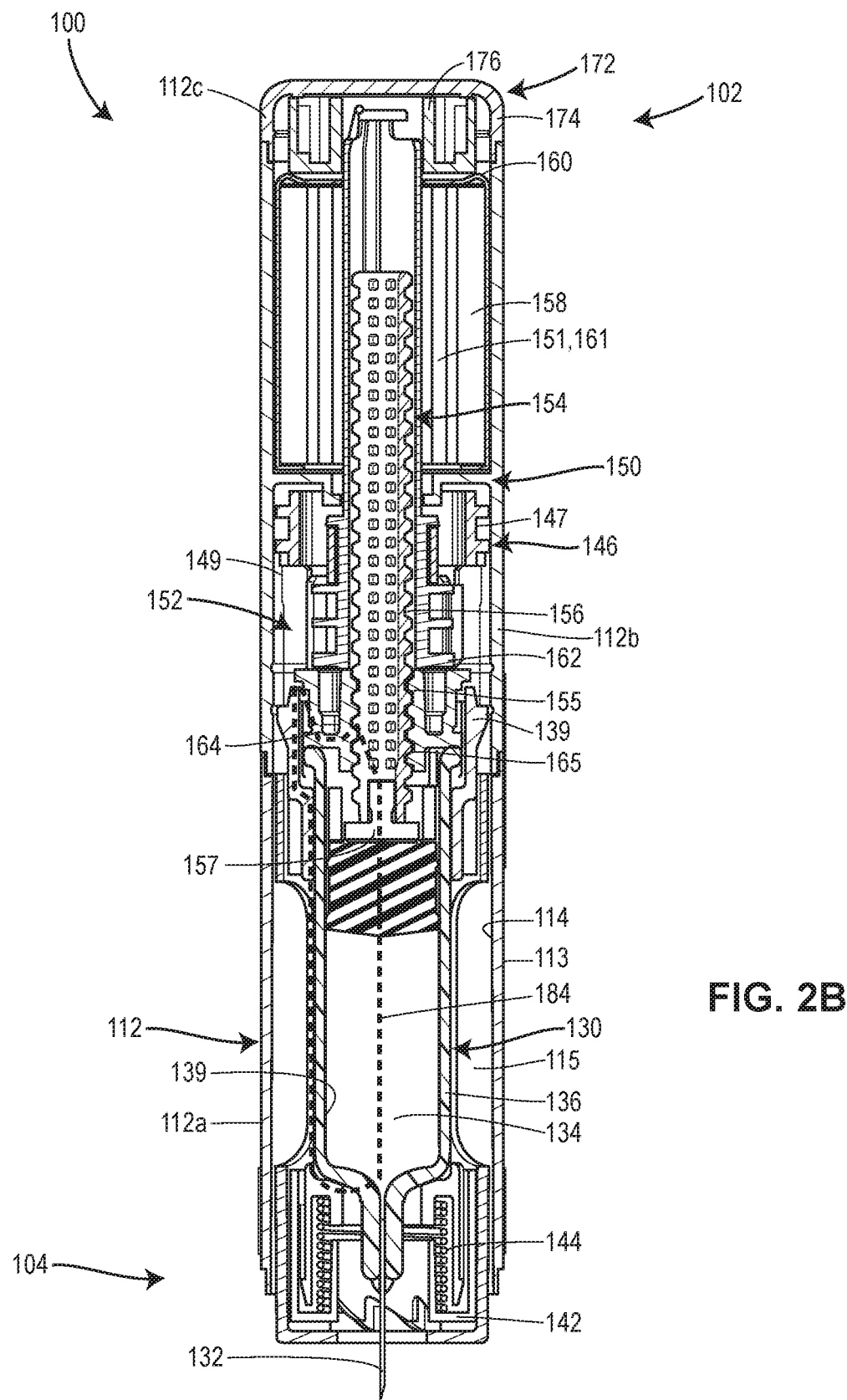
FIG. 2B is a cross-sectional view of the embodiment of the injection system of FIG. 1 in the injection state, and illustrating a third force transmission loop within the system.
Figure 2C:
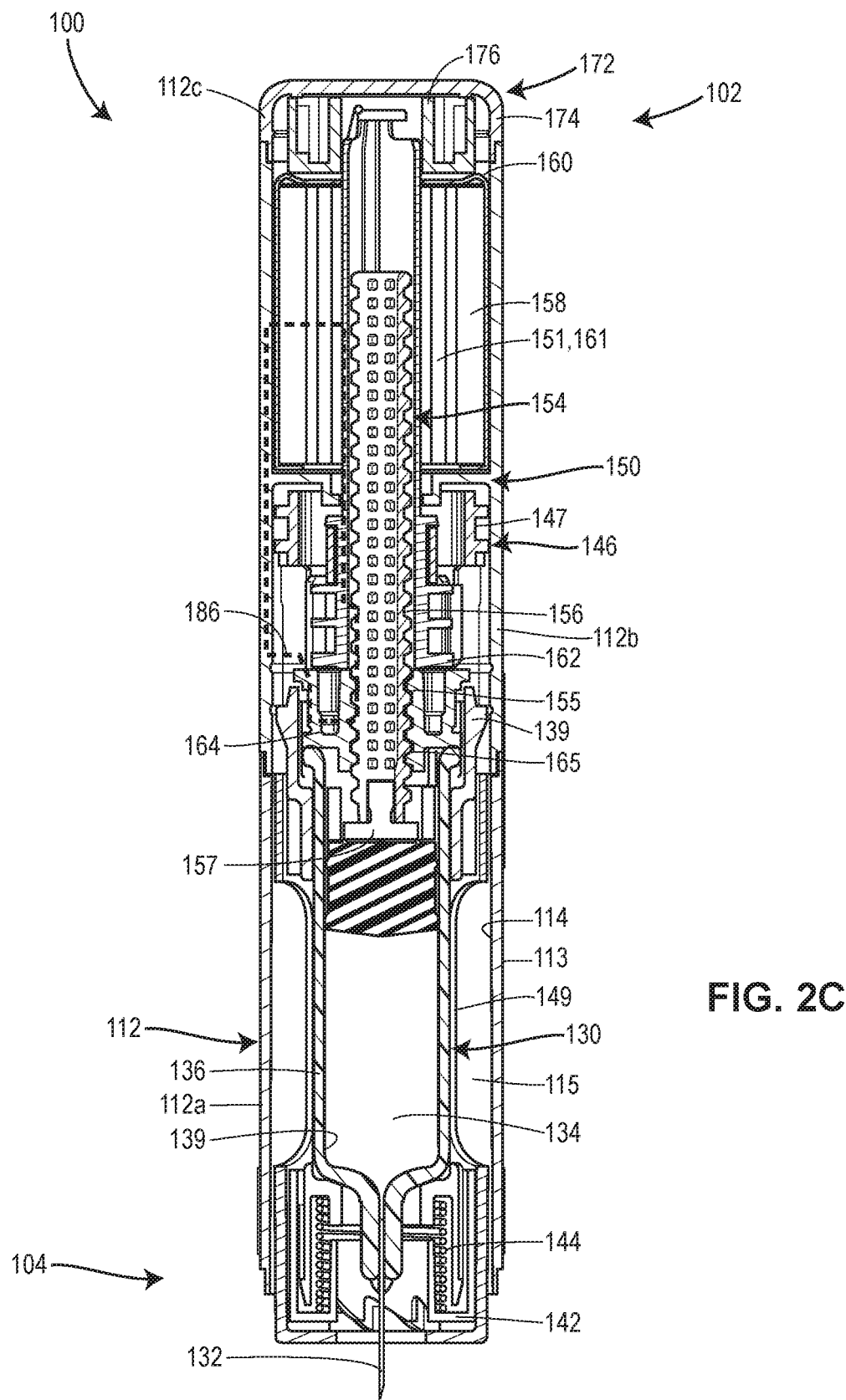
FIG. 2C is a cross-sectional view of the embodiment of the injection system of FIG. 1 in the injection state, and depicting a fourth force transmission loop within the system.

With continued reference to FIG. 1, the system 100 may also include a guard mechanism 140 for preventing the user or patient from inadvertent contact with the tip of the needle 132 prior to use. The guard mechanism 140 may include a guard member 142 movably disposed at the distal end of the outer housing 112. The guard member 142 may have a hollow and generally cylindrical or tubular shape. The guard mechanism 140 may further include a guard biasing member 144 (e.g., a spring) that urges the guard member 142 towards an extended position protruding from the outer housing 112 when the system 100 is not in use (as depicted in FIG. 1), and allows the guard member 142 to retract in the proximal direction into the interior space 115 of the outer housing 112 when the distal end 104 of the system 100 is pressed against a patient's skin (as depicted in FIG. 2A-2C). As a consequence of this retraction, the distal end of the needle 132 may be exposed and allowed to penetrate into the patient's skin.

Retraction of the guard member 142 may also have the effect of actuating of a trigger assembly 146. As depicted in FIG. 1, the trigger assembly 146 includes a trigger ring 147 and a trigger sleeve 149. The trigger sleeve 149 and the trigger ring 147 may be rigidly connected to each other such that they move jointly together with each other. While the trigger sleeve 149 and the trigger ring 147 are discrete structures in the present embodiment, in alternative embodiments the trigger sleeve 149 and the trigger ring 147 may be integrally formed with each other as a single, unitary, structure. The trigger sleeve 149 may be rigidly connected to the guard member 142 such that the two components move jointly together in the proximal direction when the distal end 104 of the system 100 is pressed against the patient's skin. The trigger sleeve 149 and/or the guard member 142 may make contact with the patient's skin to cause the retraction. Retraction of the trigger sleeve 149, in turn, pushes the trigger ring 147 in the proximal direction, as seen in FIGS. 2A-2C.

Depending on its position, the trigger ring 147 may selectively engage a mechanical linkage 152. As described below in more detail, when it is free to move or actuate, the mechanical linkage 152 transmits a force that is output by an energy source to a plunger 154 to cause the plunger 154 to act on the stopper 138 to expel the drug from the container 130. In the pre-injection state (FIG. 1), the trigger ring 147 may engage (e.g., directly contact) a component (e.g., a plunger sleeve 162) of the mechanical linkage 152 to inhibit or prevent movement of the mechanical linkage 152. In the injection state, when the trigger ring 147 is displaced in the proximal direction by retraction of the trigger sleeve 149, the trigger ring 147 may disengage from the mechanical linkage 152, thereby freeing the mechanical linkage 152 to move relative to the outer housing 112 (as seen in FIGS. 2A-2C). So configured, the trigger ring 147 functions as a lock for the mechanical linkage 152. In alternative embodiments, instead of functioning as a lock, the trigger ring 147 may function as a key that facilitates actuation of the mechanical linkage 152 when the trigger ring 147 is moved by retraction of the trigger sleeve 149. In still further alternative embodiments, the trigger sleeve 149 may be omitted, and the trigger ring 147 may be displaced by a finger/thumb-depressible push button, for example, in order to permit actuation of the mechanical linkage 152.

The system 100 may further include a drive assembly 150 that stores actuation energy and releases the actuation energy upon activation by a patient or user to drive the stopper 138 through the container 130 for expelling the drug and/or to drive the needle 132 into the patient's tissue. The drive assembly 150 may be disposed within the external housing 112, with at least part of the drive assembly 150 being disposed within the rear housing portion 112b. The drive assembly 150 may include, without limitation, an energy source 151, a mechanical linkage 152, a plunger 154, an energy source guide 158, and an energy source housing 160.

In the embodiment illustrated in FIG. 1, the plunger 154 includes a rod 155 having a threaded exterior surface 156, and a washer 157 connected to a distal end of the rod 155. The washer 157 may be rigidly connected to and in direct contact with the rod 155 such that the rod 155 and the washer 157 move together jointly during operation. In alternative embodiments, the rod 155 and the washer 157 may not be discrete components but rather integrally formed with each other as a single, unitary, structure. In the pre-injection state, the washer 157 may be spaced apart from the stopper 138 by a distance, as depicted in FIG. 1. In the injection state, the washer 157 may impact and exert a force or otherwise act on the stopper 138 to drive the stopper 138 through the reservoir 134 in the distal direction, as seen in FIGS. 2A-2C.

The energy source 151 may be configured to store mechanical, electrical, and/or chemical energy. Upon activation, the energy source 151 may release or otherwise output this energy in order to generate the motive force needed for actuating one or more components of the system 100. The energy source 151 may take any form including, but not limited to, one or more springs (e.g., a helical compression spring, a helical extension spring, a helical torsion spring, a spiral torsion spring, etc.), one or more electric motors, and/or one or more gas- or liquid-generating chemicals, or any combination thereof. In the embodiment illustrated in FIGS. 1-3B, the energy source 151 is defined by a spiral torsion spring 161, also sometimes referred to as a watch spring. In the pre-injection state, the spiral torsion spring 161 may be retained in a wound or energized state. Activation of the system 100 may release the spiral torsion spring 161 so that it can unwind to a de- or less-energized state.

According to embodiments wherein the energy source 151 includes a spring, the energy source 151 may output a biasing force in the pre-injection state and the injection state, and also optionally in the post-injection state. In other embodiments, such as where the energy source 151 comprises an electric motor, the energy source 151 may output a force only in the injection state. In the present embodiments, the force output by the spiral torsion spring 161 is a rotational force (i.e., a torque).

In some embodiments, the force output by the energy source 151 may vary in magnitude over the course of the pre-injection, injection, and/or post-injection states. In embodiments where the energy source 151 includes a spring, the force output by the energy source 151 may have a largest magnitude in the pre-injection state, then gradually decrease in magnitude over the course of the injection state, and have a smallest magnitude in the post-injection state. Also, in spring embodiments, the magnitude of the force output by the energy source 151 may be constant or un-changing in the pre-injection state and/or the post-injection state. In alternative embodiments, the force output by the energy source 151 may have a constant magnitude throughout the pre-injection, injection, and/or post-injection states.

The force output by the energy source 151 may not be aligned with the direction of travel of the stopper 138. The mechanical linkage 152 is therefore included to receive the force output by the energy source 151 and transmit that force in the direction of travel of the stopper 138, which in the present embodiment is aligned with a longitudinal axis of the container 130. In the present embodiment, the mechanical linkage 152 includes a plunger sleeve or guide 162 and a nut 164. Alternative embodiments of the mechanical linkage 152 may include fewer or additional components. The plunger sleeve 162 may have a hollow and generally cylindrical or tubular shape, and receive a proximal end of the rod 155 of the plunger 154, in at least the pre-injection state. In some embodiments, an inner diameter of the plunger sleeve 162 may be larger than an outer diameter of the plunger 154 such that the plunger sleeve 162 and the plunger 154 do not contact each other; whereas, in other embodiments, the two components may be in contact or allowed to contact each other. The nut 164 may be ring-shaped, and may receive at least a portion of the distal end of the rod 155 of the plunger 154 in the pre-injection state. The nut 164 may have a threaded interior surface 165 that threadably engages the threaded exterior surface 156 of the rod 155 of the plunger 154. By way of this threaded engagement, rotation of the nut 164 relative to the rod 155 may drive the rod 155 linearly in the distal direction. In the present embodiment the plunger sleeve 162 and the nut 164 are discrete components rigidly connected together; however, in alternative embodiments, the plunger sleeve 162 and the nut 164 may be integrally formed with each other as a single, unitary structure.

A proximal end of the plunger sleeve 162 may be directly connected to the energy source 151 such that the plunger sleeve 162 directly receives, and can be actuated by, the force output by the energy source 151. In the present embodiment, actuation of the plunger sleeve 162 by the energy source 151 involves the plunger sleeve 162 rotating about the plunger 154 in the injection state. A distal end of the plunger sleeve 162 may be rigidly connected to the nut 164 such that the plunger sleeve 162 and the nut 164 rotate together jointly in the injection state. Rotational motion of the nut 164 is converted into distal linear motion of the plunger 154 via the threaded engagement between these two components. The distal linear motion of the plunger 154 is transmitted to the stopper 138, which in turn expels the drug from the container 130 via the needle 132.

In the pre-injection state, the trigger ring 147 may lockingly engage an exterior surface of the plunger sleeve 162, thereby inhibiting or preventing the plunger sleeve 162 from rotating (see FIG. 1). In the injection state, the trigger ring 147 may be displaced to a position where it no longer engages the plunger 162, thereby allowing the plunger sleeve 162 to rotate and drive, via the nut 164, the plunger 154 in the distal linear direction (see FIGS. 2A-2C). The plunger 154 may push the stopper 138 in the distal linear direction until it is stopped at the end-of-dose position by the proximally-facing portion of the interior surface 139 of the wall 136, as depicted in FIGS. 3A and 3B. Here, the system 100 is considered to be in the post-injection state, even though the needle 132 may not yet have been removed from the patient's tissue.

While the present embodiment involves the mechanical linkage 152 converting rotational motion into linear motion, alternative embodiments, such as ones employing a compression or extension spring for the energy source, may involve the mechanical linkage receiving linear motion and outputting linear motion.

In some embodiments, the container 130, the stopper 138, the trigger ring 147, the plunger 154, the plunger sleeve 162, and/or the nut 164 may each be aligned with and/or centered about the longitudinal axis of the container 130.

The energy source housing 160 may be disposed within and rigidly connected to and in direct contact with the outer housing 112, particularly the rear housing portion 112b. In alternative embodiments, the energy source housing 160 may be positioned outside of the outer housing 112 yet still rigidly connected thereto. In such alternative embodiments, the energy source housing 160 may correspond to the rear housing portion 112b, and thus form a portion of the exterior surface of the system 100. The energy source housing 160 may possess a hollow and generally cylindrical or tubular shape, and may receive, in full or in part, the energy source guide 158 such that the energy source housing 160 surrounds or partially surrounds the energy source guide 158. The energy source housing 160 may serve as a mount for the energy source guide 158; and the energy source housing 160 and the energy source guide 158 may be rigidly connected to and in direct contact with each other such that they cannot move relative to each other. In the illustrated embodiment the energy source housing 160 and the energy source guide 158 are discrete components rigidly connected together; however, in alternative embodiments, the energy source housing 160 and the energy source guide 158 may be integrally formed with each other as a single, unitary structure.

The energy source guide 158 may possess a hollow and generally cylindrical or tubular shape, and may receive, in full or in part, the energy source 151 such that the energy source guide 158 surrounds or partially surrounds the energy source 151. The energy source 151 or a portion thereof may rotate or otherwise move relative to the energy source guide 158 during the injection state. In some embodiments, the energy source guide 158 may be in direct contact with the energy source 151, and serve as a mount for the energy source 151 to push off of.

Still referring to FIG. 1, the system 100 may in certain embodiments include a damper assembly 172. The damper assembly 172 generally functions as a shock absorber operable to absorb or dampen a shock impulse caused by the plunger 154 striking the stopper 138. This impulse, if not moderated, may shatter or break the container 130, which may be made of glass, and potentially break other components of the system 100 as well. When initially released, the output force of the energy source 151 may be at its greatest magnitude as compared to later in the plunger stroke. As a consequence, the energy source 151 may accelerate the plunger 154 to a relatively high velocity prior to the plunger 154 acting on the stopper 138. The damper assembly 172 may be operable to reduce the velocity of the plunger 154 prior to acting on the stopper 138. As illustrated in FIG. 1, the damper assembly 172 may include a damper housing 174 and a damper member 176. The damper member 176 may be fixedly connected to the plunger sleeve 162 such that two components rotate together jointly in the injection state. In some embodiments, a damping fluid may be sealed within the damper housing 174 and in contact with the damper member 176. The damping fluid may at least initially act to resist rotational motion of the damper member 176, thereby providing the intended damping effect. In alternative embodiments, the damping fluid may be omitted, and instead the damping effect may be achieved via frictional contact between the exterior surface of the damper member 176 and the interior surface of the damper housing 174.

The damper housing 174 may be disposed within and rigidly connected to and in direct contact with the outer housing 112, particularly the rearmost housing portion 112c. In alternative embodiments, the damper housing 174 may be positioned outside of the outer housing 112 and rigidly connected thereto. In such alternative embodiments, the damper housing 174 may correspond to the rearmost housing portion 112c, and thus form a portion of the exterior surface of the system 100. The damper housing 174 may possess a hollow and generally cylindrical or tubular shape, and may receive, in full or in part, the damper member 176 such that the damper housing 174 surrounds or partially surrounds the damper member 176. While the damper member 176 may be able to rotate relative to the damper housing 174, other degrees of freedom of the damper member 176 may be restricted.

In some embodiments, the damper member 176 may be ring-shaped and receive a portion of the proximal end of the plunger sleeve 162, as illustrated in FIG. 1. An interior surface of the damper member 176 may directly and slidably contact the exterior surface of the plunger sleeve 162. Friction between these two surfaces during the injection state may provide the desired damping effect. Other embodiments may additionally or alternatively rely on a shock absorbing material and/or hydraulic fluid to provide the desired damping effect.

While the present disclosure describes and/or illustrates certain components of the system 100 as being separate, discrete elements, it should be understood that in some embodiments such components may be integrally formed with each other as a single, unitary structure, including components described and/or illustrated as being in direct contact with and/or rigidly connected to each other, so long as such components are not required to move relative to each other during use or operation of the system 100.

Having described the configuration and operation of the system 100, now the advantageous mechanics and force characteristics of the system 100 will be described. Basic physics teaches that all forces occur in pairs such that if one object exerts a force on another object, then the second object exerts an equal and opposite reaction force on the first object. If the second object transmits the force to a third object, then the third object exerts an equal and opposite reaction force on the second object, and so on and so forth for additional objects to which the force is transmitted. If the objects are operably connected in series (i.e., one after the other), and the first object and the last object are operably connected to each other, a force transmission loop may be formed. The applied force and any reaction forces induced by the applied force may act along the force transmission loop. If it is only the objects operably connected in series that bear the applied force and any reaction forces, the force transmission loop may be considered to be closed. By contrast, if there is an additional object that receives a force from the force transmission loop but this additional object is not operably connected in series with the other objects, the force transmission loop may be considered to be open. Here, the additional object may move relative to the other objects as a consequence of receiving a force from the force transmission loop.

Various force transmission loops may be present within the injection system 100 during the pre-injection state, the injection state, and/or the post-injection state. As compared to conventional injection systems, the system 100 is configured with less components exposed to the force transmission loops, which can provide more freedom in the design and/or manufacture of the system 100. Stated another way, the force transmission loops existing in the system 100 may be shorter than equivalent force transmission loops found in conventional injection systems.

In certain embodiments, the entirety of the outer housing 112, or at least the front housing portion 112a, may be excluded from any and all of the force transmission loops in any and all of the pre-injection, injection, and post-injection states. As such, the outer housing 112, or at least the front housing portion 112a, may be substantially free of or may not be required to bear any load or mechanical stress directly or indirectly caused by the force output by the energy source 151. Therefore, there may be more flexibility in the design and/or manufacture of the outer housing 112, or at least the front housing portion 112a.

The force transmission loops may directly or indirectly receive the force output by the energy source 151. As described below in more detail, certain force transmission loops may include the energy source 151 operably connected in series with other components. Other force transmission loops, by contrast, may not include the energy source 151. Such force transmission loops may nevertheless indirectly receive the force output by the energy source 151.

Referring to FIG. 1, in the pre-injection state, the system 100 may have a first force transmission loop 180 (illustrated in dotted lines). The first force transmission loop 180 may, in certain embodiments, directly receive the force output by the energy source 151. At least the energy source 151, the plunger sleeve 162, the trigger ring 147, the nut 164, the energy source housing 160, and the energy source guide 158 may be operably connected (e.g., directly connected or indirectly connected) in series to define the first force transmission loop 180. At least the front housing portion 112a may be excluded from the first force transmission loop 180, although in some embodiments the entire outer housing 112 may be excluded from the first force transmission loop 180. In some embodiments, the first force transmission loop 180 may be restricted to (i.e., exclusive to) the operable connection among the energy source 151, the plunger sleeve 154, the trigger ring 147, the nut 164, the energy source hosing 160, and the energy source guide 158. In such embodiments, the first transmission loop 180 may be achieved by configuring, in the pre-injection state: the energy source 151 in direct contact with to the plunger sleeve 162, the plunger sleeve 162 in direct contact with the trigger ring 147, the trigger ring 147 in direct contact with the nut 164, the nut 164 in direct contact with the energy source housing 160, the energy source housing 160 in direct contact with the energy source guide 158, and the energy source guide 158 in direct contact with the energy source 151.

Turning to FIGS. 2A-2C, various force transmission loops present in the injection state will now be described. FIG. 2A illustrates a second force transmission loop 182 (illustrated in dotted lines) that is present in the injection state. The second force transmission loop 182 may, in certain embodiments, directly receive the force output by the energy source 151. At least the energy source 151, the plunger sleeve 162, the damper member 176, the damper housing 174, and the energy source guide 158 may be operably connected in series to define the second force transmission loop 182. At least the front housing portion 112a may be excluded from the second force transmission loop 182, although in some embodiments the entire outer housing 112 may be excluded from the second force transmission loop 182. In some embodiments, the second force transmission loop 182 may be restricted to the operable connection among the energy source 151, the plunger sleeve 162, the damper member 176, the damper housing 174, and the energy source guide 158. In such embodiments, the second transmission loop 182 may be achieved by configuring, in the injection state: the energy source 151 in direct connect with the plunger sleeve 154, the plunger sleeve 154 in direct contact with the damper member 176, the damper member 176 in direct contact with the damper housing 174, the damper housing 174 in direct contact with the energy source guide 158, and the energy source guide 158 in direct contact with the energy source 151. In some embodiments, in lieu of direct contact between the damper member 176 and the damper housing 174, the damper member 176 may be operably connected to the damper housing 174 via the damping fluid mentioned above.

FIG. 2B illustrates a third force transmission loop 184 (illustrated in dotted lines) that is present in the injection state. The third force transmission loop 184 may, in certain embodiments, indirectly receive the force output by the energy source 151. At least the nut 164, the plunger 154, the stopper 138, the container 130, and the container holder 139 may be operably connected in series to define the third force transmission loop 184. At least the front housing portion 112a may be excluded from the third transmission loop 184, although in some embodiments the entire outer housing 112 may be excluded from the second force third loop 184. In some embodiments, the third force transmission loop 184 may be restricted to the operable connection among the nut 164, the plunger 154, the stopper 138, the container 130, and the container holder 139. In such embodiments, the third transmission loop 184 may be achieved by configuring, in the injection state: the nut 164 in direct contact with the plunger 154, the plunger 154 in direct contact with the stopper 138, the stopper 138 in direct contact with the container 130, the container 130 in direct contact with the container holder 139, and the container holder 139 in direct contact with the nut 164.

FIG. 2C illustrates a fourth force transmission loop 186 (illustrated in dotted lines) that is present in the injection state. The fourth force transmission loop 186 may, in certain embodiments, directly receive the force output by the energy source 151. At least the energy source 151, the plunger sleeve 162, the plunger 154, the nut 164, the energy source housing 160, the energy source guide 158 may be operably connected in series to define the fourth force transmission loop 186. At least the front housing portion 112a may be excluded from the fourth transmission loop 186, although in some embodiments the entire outer housing 112 may be excluded from the fourth transmission loop 186. In some embodiments, the fourth transmission loop 186 may be restricted to the operable connection among the energy source 151, the plunger sleeve 162, the plunger 154, the nut 164, the energy source housing 160, and the energy source guide 158. In such embodiments, the fourth transmission loop 186 may be achieved by configuring, in the injection state: the energy source 151 in direct contact with the plunger sleeve 162, the plunger sleeve 162 in direct contact with the plunger 154, the plunger 154 in direct contact with the nut 164, the nut 164 in direct contact with the energy source housing 160, the energy source housing 160 in direct contact with the energy source guide 158, and the energy source guide 158 in direct contact with the energy source 151.

Referring now to FIGS. 3A and 3B, various force transmission loops present in the post-injection state will now be described. FIG. 3A illustrates a fifth force transmission loop 188 (illustrated in dotted lines) that is present in the post-injection state. The fifth force transmission loop 188 may, in certain embodiments, indirectly receive the force output by the energy source 151. At least the nut 164, the plunger 154, the stopper 138, the container 130, and the container holder 139 may be operably connected in series to define the fifth force transmission loop 188. At least the front housing portion 112a may be excluded from the fifth force transmission loop 188, although in some embodiments the entire outer housing 112 may be excluded from the fifth transmission loop 188. In some embodiments, the fifth force transmission loop 188 may be restricted to the operable connection among the nut 164, the plunger 154, the stopper 138, the container 130, and the container holder 139. In such embodiments, the fifth force transmission loop 188 may be achieved by configuring, in the post-injection state: the nut 164 in direct contact with the plunger 154, the plunger 154 in direct contact with the stopper 138, the stopper 138 in direct contact with the container 130, the container 130 in direct contact with the container holder 139, and the container holder 139 in direct contact with the nut 164.

FIG. 3B illustrates a sixth force transmission loop 190 (illustrated in dotted lines) that is present in the post-injection state. The sixth force transmission loop 190 may, in certain embodiments, directly receive the force output by the energy source 151. At least the energy source 151, the plunger sleeve 162, the plunger 154, the nut 164, the energy source housing 160, and the energy source guide 158 may be operably connected in series to define the sixth force transmission loop 190. At least the front housing portion 112a may be excluded from the sixth force transmission loop 190, although in some embodiments the entire outer housing 112 may be excluded from the sixth force transmission loop 190. In some embodiments, the sixth force transmission loop 190 may be restricted to the operable connection among the energy source 151, the plunger sleeve 162, the plunger 154, the nut 164, the energy source housing 160, and the energy source guide 158. In such embodiments, the sixth force transmission loop 190 may be achieved by configuring, in the post-injection state: the energy source 151 in direct contact with the plunger sleeve 162, the plunger sleeve 162 in direct contact with the plunger 154, the plunger 154 in direct contact with the nut 164, the nut 164 in direct contact with the energy source housing 160, the energy source housing 160 in direct contact with the energy source guide 158, and the energy source guide 158 in direct contact with the energy source 151.

Figure 4:
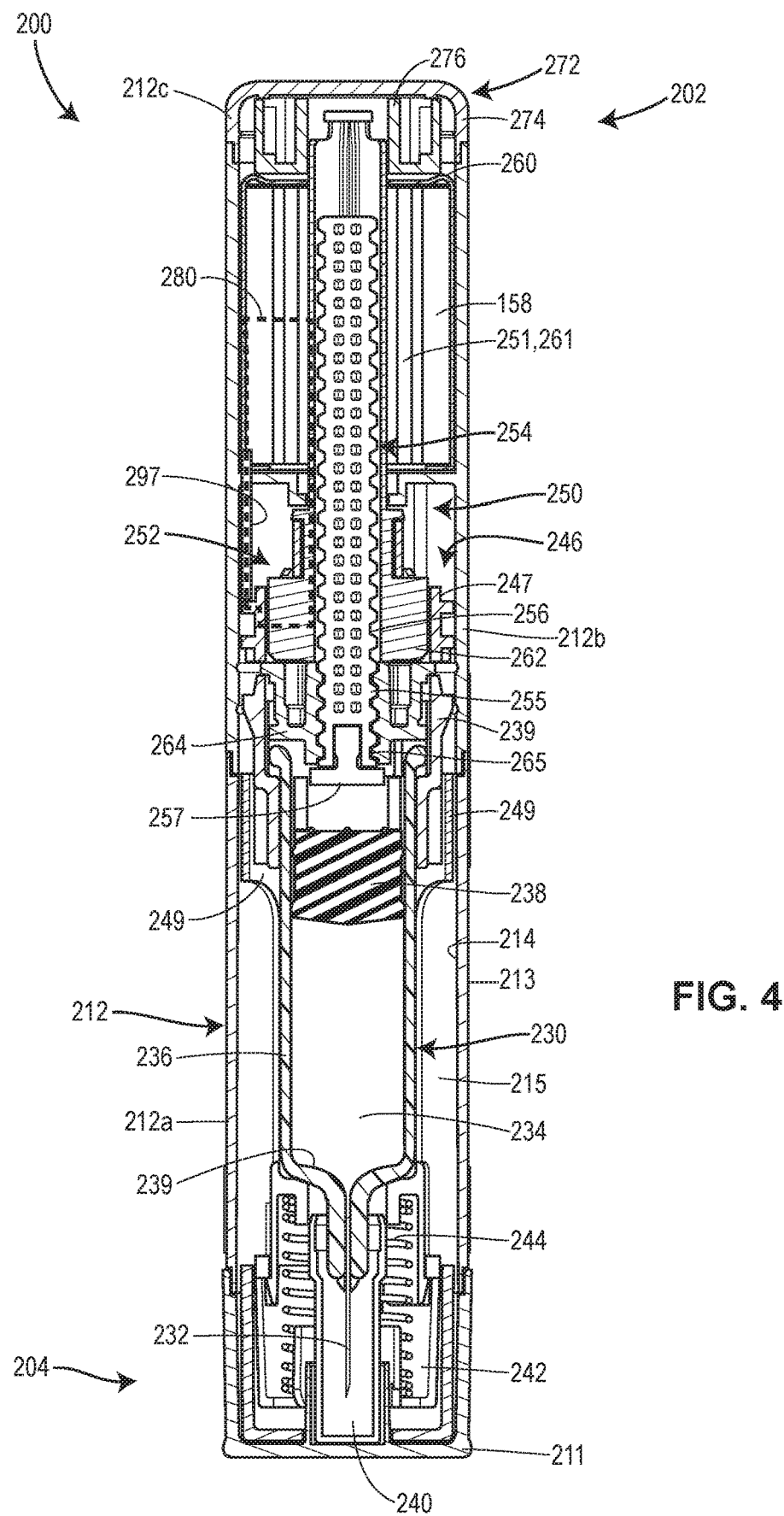
FIG. 4 is a cross-sectional view of an injection system for drug delivery in a pre-injection state according to an alternative embodiment of the present disclosure, and illustrating an alternate version of the first force transmission loop within the system.

Referring now to FIG. 4, illustrated is the pre-injection state of an alternative embodiment of the system 100. Here, the group of components defining the first force transmission loop differs from the group of components defining the first force transmission loop described in connection with the embodiment of FIG. 1. Elements of the system depicted in FIG. 4 which are the same as or similar to those of the system depicted in FIG. 1 are designated by the same reference numeral, incremented by 100. A description of many of these elements is abbreviated or even eliminated in the interest of conciseness.

A structural difference between the system 200 and the system 100 is that the trigger ring 247 is directly connected to the energy source guide 258 via an extension member 297, which may be integrally formed with the trigger ring 247 or the energy source guide 258. As a consequence, forces can be transmitted directly between the trigger ring 247 and the energy source guide 258 via the extension member 297. By contrast, in the system 100, the trigger ring 147 is connected to the energy source guide 158 via the energy source housing 160. In the system 200, the energy source housing 260 may be excluded from the first force transmission loop 280 (illustrated in dotted lines in FIG. 4). Thus, in the system 200, the energy source housing 260 may be substantially free of or may not be required to bear any load or mechanical stress caused by the force output by the energy source 251.

More particularly with respect to the embodiment of FIG. 4, at least the energy source 251, the plunger sleeve 262, the trigger ring 247, the nut 264, and the energy source guide 258 may be operably connected in series to define the first force transmission loop 280 in the pre-injection state. In some embodiments, the first force transmission loop 280 may be restricted to the operable connection among the energy source 251, the plunger sleeve 254, the trigger ring 247, the nut 264, and the energy source guide 258. In such embodiments, the first transmission loop 280 may be achieved by configuring, in the pre-injection state: the energy source 251 in direct contact with to the plunger sleeve 262, the plunger sleeve 262 in direct contact with the trigger ring 247, the trigger ring 247 in direct contact with the nut 264, the nut 264 in direct contact with the energy source guide 258, and the energy source guide 258 in direct contact with the energy source 251.

Figure 5:
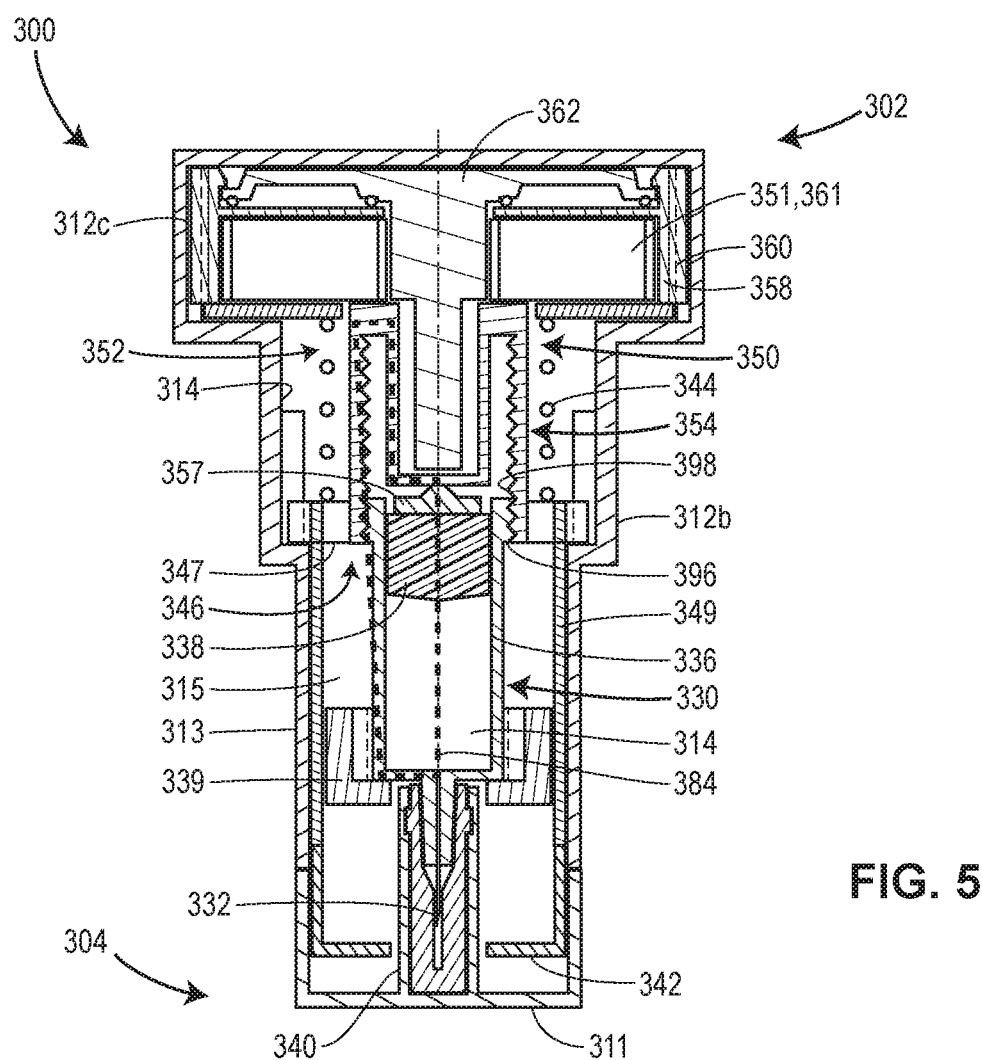
FIG. 5 is a cross-sectional view of an injection system for drug delivery in an injection state according to an alternative embodiment of the present disclosure, and illustrating an alternate version of the third force transmission loop within the system.

Turning to FIG. 5, illustrated is an injection state of an alternative embodiment of the system 100. Here, the group of components defining the third force transmission loop differs from the group of components defining the third force transmission loop described in connection with the embodiment of FIG. 2B. Elements of the system depicted in FIG. 5 which are the same as or similar to those of the system depicted in FIG. 2B are designated by the same reference numeral, incremented by 200. A description of many of these elements is abbreviated or even eliminated in the interest of conciseness.

Several structural differences exist between the system 300 and the system 100. The plunger 354 of the system 300 does not include an exterior surface that is threadably engaged with an interior surface of a nut. Rather, the plunger 354 has a threaded interior surface 395 that threadably engages a threaded exterior surface 396 of the container 330. The threaded interior surface 395 of the plunger 354 and the threaded exterior surface 396 of the container 330 may collectively define the mechanical linkage of the system 300. Another difference is that the trigger ring 347 selectively engages a portion of the exterior the plunger 354 to control actuation plunger 354. In the injection state, when the trigger ring 347 has disengaged from the plunger 354, the plunger 354 may rotate under the force output by the energy source 351, which in turn, via the threaded engagement between the surfaces 395 and 396, may cause distal linear motion of the plunger 354.

With continued reference to FIG. 5, at least the plunger 354, the stopper 338, and the container 330 may be operably connected in series to define the third force transmission loop 384 (illustrated in dotted lines in FIG. 5) in the injection state. In some embodiments, the third force transmission loop 384 may be restricted to the operable connection among the plunger 354, the stopper 338, and the container 330. In such embodiments, the third force transmission loop 384 may be achieved by configuring, in the injection state: the plunger 354 in direct contact with the stopper 338, the stopper 338 in direct contact with the container 330, and the container 330 in direct contact with the plunger 354.

Figure 6:
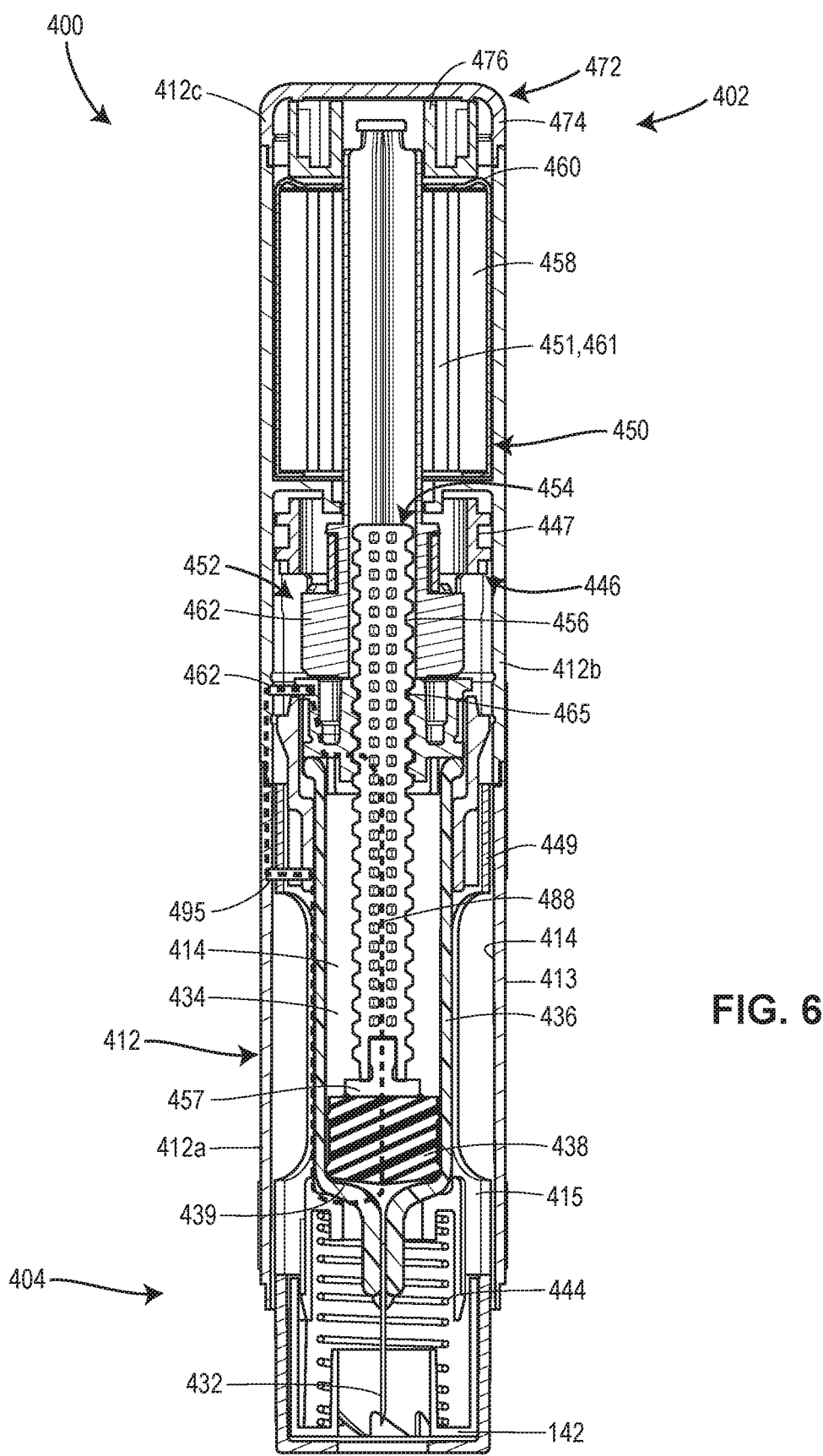
FIG. 6 is a cross-sectional view of an injection system for drug delivery in a post-injection state according to an alternative embodiment of the present disclosure, and depicting an alternate version of the fifth force transmission loop within the system.

Turning to FIG. 6, illustrated is a post-injection state of an alternative embodiment of the system 100. Here, the group of components defining the fifth force transmission loop differs from the group of components defining the fifth force transmission loop described in connection with the embodiment of FIG. 3A. Elements of the system depicted in FIG. 6 which are the same as or similar to those of the system depicted in FIG. 3A are designated by the same reference numeral, incremented by 300. A description of many of these elements is abbreviated or even eliminated in the interest of conciseness.

Several structural differences exist between the system 400 and the system 100. In the system 100, the container holder 139 is able to directly transmit forces to the nut 164. By contrast, in the system 400, the container holder 439 transmits forces to the nut 164 via a connector member 495, the front housing portion 412a, the rear housing portion 412b, and a connector member 496. The container holder 439 and the connector member 495 may be integrally formed as a single, unitary structure, or as a two separate but rigidly connected parts. The nut 164 and the connector member 496 may integrally formed as a single, unitary structure, or a two separate but rigidly connected parts.

With continued reference to FIG. 6, at least the nut 464, the plunger 454, the stopper 438, the container 430, the container holder 439, the front housing portion 412a, and the rear housing portion 412b may be operably connected in series to define the fifth force transmission loop 488 (illustrated in dotted lines) in the post-injection state. In some embodiments, the fifth force transmission loop 488 may be restricted to the operable connection among the nut 464, the plunger 454, the stopper 438, the container 430, the container holder 439, the front housing portion 412a, and the rear housing portion 412b. In such embodiments, the fifth force transmission loop 488 may be achieved by configuring, in the post-injection state: the nut 464 in direct contact with the plunger 454, the plunger 454 in direct contact with the stopper 438, the stopper 438 in direct contact with the container 430, the container 430 in direct contact with the container holder 439, the container holder 439 in direct contact with the front housing portion 412a, the front housing portion 412a in direct contact with the rear housing portion 412b, and the rear housing portion 412b in direct contact with nut 464.

Figure 7:
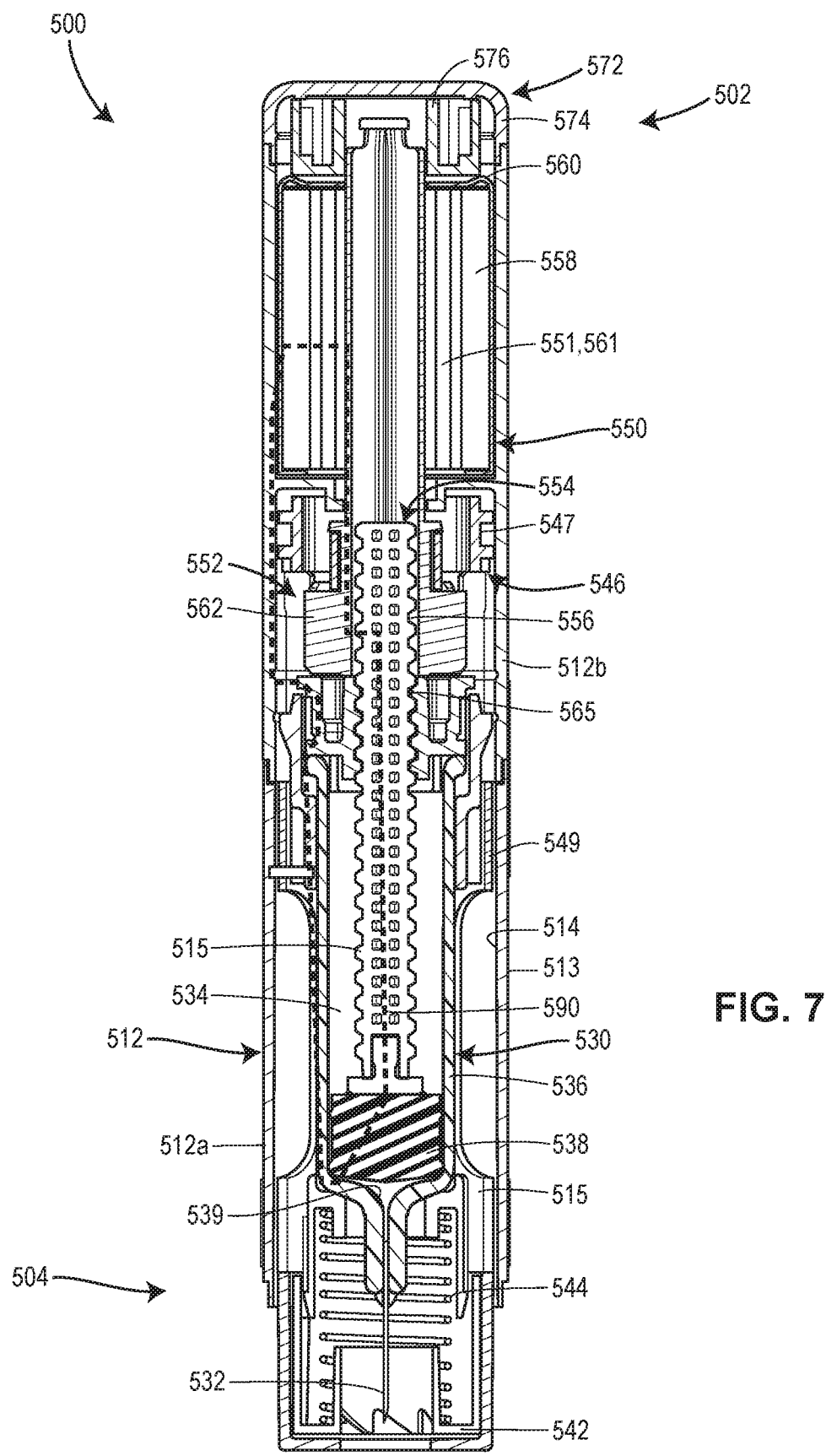
FIG. 7 is a cross-sectional view of an injection system for drug delivery in a post-injection state according to an alternative embodiment of the present disclosure, and illustrating an alternate version of the sixth force transmission loop within the system.

Turning to FIG. 7, illustrated is a post-injection state of another alternative embodiment of the system 100. Here, the group of components defining the sixth force transmission loop differs from the group of components defining the sixth force transmission loop described in connection with the embodiment of FIG. 3B. Elements of the system depicted in FIG. 7 which are the same as or similar to those of the system depicted in FIG. 3B are designated by the same reference numeral, incremented by 400. A description of many of these elements is abbreviated or even eliminated in the interest of conciseness.

With continued reference to FIG. 7, at least the energy source 551, the plunger sleeve 562, the plunger 554, the stopper 538, the container 530, the container holder 539, the nut 564, the energy source housing 560, and the energy source guide 558 may be operably connected in series to define the sixth force transmission loop 590 (illustrated in dotted lines) in the post-injection state.

In some embodiments, the sixth force transmission loop 590 may be restricted to the operable connection among the energy source 551, the plunger sleeve 562, the plunger 554, the stopper 538, the container 530, the container holder 539, the nut 564, the energy source housing 560, and the energy source guide 558.

In such embodiments, the sixth force transmission loop 590 may be achieved by configuring, in the post-injection state: the energy source 551 in direct contact with the plunger sleeve 562, the plunger sleeve 562 in direct contact with the plunger 554, the plunger 554 in direct contact with the stopper 538, the stopper 538 in direct contact with the container 530, the container 530 in direct contact with the container holder 539, the container holder 539 in direct contact with the nut 564, the nut 564 in direct contact with the energy source housing 560, the energy source housing 560 in direct contact with the energy source guide 558, and the energy source guide 558 in direct contact with the energy source 551.

As will be recognized, the systems, devices, and methods according to the present disclosure may have one or more advantages relative to conventional technology, any one or more of which may be present in a particular embodiment in accordance with the features of the present disclosure included in that embodiment. Other advantages not specifically listed herein may also be recognized as well.

Drug Information

The above description describes various assemblies, devices, and methods for use with a drug delivery device. It should be clear that the assemblies, drug delivery devices, or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of sequence identification number 2 as set forth therein in FIG. 2 and/or the heavy chain of sequence identification number 4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of sequence identification numbers 305-351, including TN8-19-1 through TN8-19-40, TN8-19 con1 and TN8-19 con2; peptibodies of the mL2 family of sequence identification numbers 357-383; the mL15 family of sequence identification numbers 384-409; the mL17 family of sequence identification numbers 410-438; the mL20 family of sequence identification numbers 439-446; the mL21 family of sequence identification numbers 447-452; the mL24 family of sequence identification numbers 453-454; and those of sequence identification numbers 615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6;

L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody*7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/ 19D12 LCF (K), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences designated therein as, respectively, sequence identification number 1 and sequence identification number 7); 5D (having light chain variable and heavy chain variable sequences designated therein as, respectively, sequence identification number 2 and sequence identification number 9); 2H (having light chain variable and heavy chain variable sequences designated therein as, respectively, sequence identification number 3 and sequence identification number 10); 43H (having light chain variable and heavy chain variable sequences designated therein as, respectively, sequence identification number 6 and sequence identification number 14); 41H (having light chain variable and heavy chain variable sequences designated therein as, respectively, sequence identification number 5 and sequence identification number 13); and 15H (having light chain variable and heavy chain variable sequences designated therein as, respectively, sequence identification number 4 and sequence identification number 12), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of sequence identification number 17 and the light chain of sequence identification number 18; those having the heavy chain variable region of sequence identification number 6 and the light chain variable region of sequence identification number 8; those having the heavy chain of sequence identification number 19 and the light chain of sequence identification number 20; those having the heavy chain variable region of sequence identification number 10 and the light chain variable region of sequence identification number 12; those having the heavy chain of sequence identification number 32 and the light chain of sequence identification number 20; those having the heavy chain variable region of sequence identification number 30 and the light chain variable region of sequence identification number 12; those having the heavy chain sequence of sequence identification number 21 and the light chain sequence of sequence identification number 22; those having the heavy chain variable region of sequence identification number 14 and the light chain variable region of sequence identification number 16; those having the heavy chain of sequence identification number 21 and the light chain of sequence identification number 33; and those having the heavy chain variable region of sequence identification number 14 and the light chain variable region of sequence identification number 31, as disclosed in the foregoing publication. A specific antibody contemplated is antibody 1119 as disclosed in the foregoing U.S. publication and having a complete heavy chain of sequence identification number 17 as disclosed therein and having a complete light chain of sequence identification number 18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686, 292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising sequence identification number 8 and a light chain variable region having sequence identification number 6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar@ (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4 integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery devices, methods, and components thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention. For example, components described herein with reference to certain kinds of drug delivery devices, such as on-body injector drug delivery devices or other kinds of drug delivery devices, can also be utilized in other kinds of drug delivery devices, such as autoinjector drug delivery devices.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A system for injecting a drug, comprising:
an outer housing defining an interior space and configured to be held by a patient or user during an injection;
a container filled or fillable with the drug, at least a portion of the container being disposed in the interior space of the outer housing;
a stopper movably disposed in the container for expelling the drug from the container;
a plunger for acting on the stopper;
an energy source outputting or operable to output a force, at least a portion of the energy source being disposed in the interior space of the outer housing;
a mechanical linkage operable to transmit the force output by the energy source to the plunger to cause the plunger to act on the stopper to expel the drug;
a trigger member selectively engageable with the mechanical linkage to control actuation of the mechanical linkage;
the system having a pre-injection state, wherein the trigger member inhibits actuation of the mechanical linkage, and an injection state, wherein the trigger member permits actuation of the mechanical linkage; and
wherein at least a portion of the outer housing is substantially free of any load directly or indirectly caused by the force output by the energy source in the pre-injection state and/or the injection state.

2. The system of claim 1, wherein, in the pre-injection state, at least the energy source, the plunger, the mechanical linkage, and the trigger member are operably connected in series to define a first force transmission loop, the first force transmission loop directly or indirectly receiving the force output by the energy source.

3. The system of claim 1, the mechanical linkage including a nut and a plunger sleeve, the nut threadably engaging the plunger and being operably connected to the energy source via the plunger sleeve, the plunger sleeve receiving at least a portion of the plunger in the pre-injection state.

4. The system of claim 1, comprising an energy source guide receiving at least a portion of the energy source, and the mechanical linkage including a plunger sleeve receiving at least a portion of the plunger.

5. The system of claim 1, the plunger having a threaded interior surface threadably engaging a threaded exterior surface of the container.

6. The system of claim 1, comprising:
the mechanical linkage including a plunger sleeve receiving at least a portion of the plunger;

a damper operable to reduce a velocity of the plunger prior to acting on the stopper;
a damper housing receiving at least a portion of the damper;
an energy source guide receiving at least a portion of the energy source; and
an energy source housing receiving at least a portion of the energy source guide.

7. The system of claim 6, comprising:
the mechanical linkage including a nut threadably engaging the plunger; and
a container holder receiving at least a portion of the container.

8. The system of claim 1, comprising:
the mechanical linkage including a nut threadably engaging the plunger;
a container holder receiving at least a portion of the container; and
wherein the system has a post-injection state, wherein the plunger is stationarily positioned in an end-of-dose position, and wherein at least the portion of the outer housing does not bear any load caused by the force output by the energy source in the pre-injection state, the injection state, and/or the post-injection state.

9. The system of claim 1, comprising:
the mechanical linkage including a nut and a plunger sleeve, the nut threadably engaging the plunger and being operably connected to the energy source via the plunger sleeve;
an energy source guide receiving at least a portion of the energy source;
an energy source housing receiving at least a portion of the energy source guide; and
wherein the system has a post-injection state wherein the plunger is stationarily positioned in an end-of-dose position.

10. The system of claim 1, wherein at least the portion of the outer housing does not bear any load caused by the force output by the energy source in the pre-injection state and/or the injection state.

11. A system for injecting a drug, comprising:
a housing defining at least a portion of an exterior surface of the system;
a container filled or fillable with the drug, at least a portion of the container being disposed in the housing;
a stopper movably disposed in the container for expelling the drug from the container;
a plunger for acting on the stopper;
an energy source outputting or operable to output a force, at least a portion of the energy source being disposed in the housing;
a mechanical linkage operable to transmit the force output by the energy source to the plunger to cause the plunger to act on the stopper to expel the drug;
a trigger member selectively engageable with the mechanical linkage to control actuation of the mechanical linkage;
the system having a pre-injection state, wherein the trigger member inhibits actuation of the mechanical linkage, and an injection state, wherein the trigger member permits actuation of the mechanical linkage; and
wherein, in the pre-injection state, at least the energy source, the plunger, the mechanical linkage, and the trigger member are operably connected in series to define a first force transmission loop, wherein the first force transmission loop directly or indirectly receives the force output by the energy source, and wherein at least a portion of the housing is excluded from the first force transmission loop in the pre-injection state such that at least the portion of the housing is substantially free of any load directly or indirectly caused by the force output by the energy source in the pre-injection state.

12. The system of claim 11, wherein, in the pre-injection state, the first force transmission loop is restricted to the operable connection among the energy source, the plunger, and the mechanical linkage.

13. The system of claim 11, comprising:
the mechanical linkage including a nut and a plunger sleeve, the nut threadably engaging the plunger and being operably connected to the energy source via the plunger sleeve, the plunger sleeve receiving at least a portion of the plunger in the pre-injection state;
an energy source guide receiving at least a portion of the energy source; and
an energy source housing receiving at least a portion of the energy source guide.

14. The system of claim 11, comprising:
an energy source guide receiving at least a portion of the energy source; and
the mechanical linkage including a plunger sleeve receiving at least a portion of the plunger.

15. The system of claim 11, the plunger threadably engaging a threaded exterior surface of the container.

16. The system of claim 11, comprising:
the mechanical linkage including a plunger sleeve receiving at least a portion of the plunger;
a damper operable to reduce a velocity of the plunger prior to acting on the stopper;
a damper housing receiving at least a portion of the damper;
an energy source guide receiving at least a portion of the energy source; and
an energy source housing receiving at least a portion of the energy source guide.

17. The system of claim 11, comprising:
the mechanical linkage including a nut threadably engaging the plunger; and
a container holder receiving at least a portion of the container.

18. The system of claim 11, comprising:
the mechanical linkage including a nut threadably engaging the plunger;
a container holder receiving at least a portion of the container; and
wherein the system has a post-injection state wherein the plunger is stationarily positioned in an end-of-dose position.

19. The system of claim 11, comprising:
the mechanical linkage including a nut and a plunger sleeve, the nut threadably engaging the plunger and being operably connected to the energy source via the plunger sleeve;
an energy source guide receiving at least a portion of the energy source;
an energy source housing receiving at least a portion of the energy source guide; and
wherein the system has a post-injection state wherein the plunger is stationarily positioned in an end-of-dose position.

20. The system of claim 11, comprising:
a nut threadably engaging the plunger;
a container holder receiving at least a portion of the container;

a front housing receiving at least a portion of the container holder; and a rear housing receiving at least a portion of the energy source; and wherein the system has a post-injection state wherein the plunger is stationarily positioned in an end-of-dose position.

21. The system of claim 1, wherein the outer housing includes at least a front portion and a rear portion, and wherein at least the portion of the outer housing includes the front portion of the outer housing.

22. The system of claim 21, wherein at least the front portion of the outer housing is excluded from one or more force transmission loops such that at least the front portion of the outer housing is substantially free of any load directly or indirectly caused by the force output by the energy source in the pre-injection state and/or the injection state.

23. The system of claim 22, wherein two or more components in the interior space of the outer housing are operably connected in series to define the one or more force transmission loops.

24. The system of claim 11, wherein the housing includes at least a front portion and a rear portion, and wherein at least the portion of the housing includes the front portion of the housing.

25. A system for injecting a drug, comprising:

an outer housing defining an interior space;

a container filled or fillable with the drug, at least a portion of the container being disposed in the interior space of the outer housing;

a stopper movably disposed in the container for expelling the drug from the container;

a plunger for acting on the stopper; and an energy source outputting or operable to output a force, at least a portion of the energy source being disposed in the interior space of the outer housing;

wherein at least a portion of the outer housing is excluded from one or more force transmission loops such that at least the portion of the outer housing is substantially free of any load caused by the force output by the energy source in the pre-injection state and/or the injection state, and wherein two or more components disposed in the interior space of the outer housing are operably connected in series to define the one or more force transmission loops.

26. The system of claim 25, wherein outer housing includes at least a front portion and a rear portion, and wherein at least the portion of the outer housing includes the front portion of the outer housing.

27. The system of claim 1, wherein the container is filled or pre-filled with the drug, and wherein the drug comprises evolocumab.

28. The system of claim 11, wherein the container is filled or pre-filled with the drug, and wherein the drug comprises evolocumab.

29. The system of claim 25, wherein the container is filled or pre-filled with the drug, and wherein the drug comprises evolocumab.

* * * * *